United States Patent [19]
Stein et al.

[11] Patent Number: 5,491,060
[45] Date of Patent: Feb. 13, 1996

[54] **MUTANT STRAIN OF *E. COLI* FOR DETECTION OF METHYLTRANSFERASE CLONES**

[75] Inventors: Daniel C. Stein, Silver Spring; Andrejez S. Piekarowicz, Adelphi; Robert T. Yuan, Gaithersburg, all of Md.

[73] Assignee: The University of Maryland, College Park, Md.

[21] Appl. No.: 956,578

[22] Filed: Oct. 6, 1992

Related U.S. Application Data

[63] Continuation of Ser. No. 345,292, May 1, 1989, abandoned.

[51] Int. Cl.$^6$ .............................. C12Q 1/68; C12N 15/09; C12N 15/54; C12N 15/55
[52] U.S. Cl. ..................... 435/6; 435/172.3; 435/193; 435/199; 435/252.33; 435/252.8
[58] Field of Search ................................ 435/172.3, 193, 435/199, 252.33, 252.8

[56] References Cited

U.S. PATENT DOCUMENTS 4,987,074  1/1991  Lunnen ................................ 435/172.3

OTHER PUBLICATIONS

Raleigh et al., Proc. Natl. Acad. Sci. USA, vol. 83, pp. 9070–9074 (1986).
Lewin, Genes, John Wiley and Sons, New York, 2nd edition, (1985).
Slatco et al., Gene, 74, pp. 45–50 (1988).
Wu et al., Nucleic Acids Research, vol. 16, No. 2, pp. 703–717 (Jan. 25, 1988).
Hopwood et al., in Methods in Microbiology, vol. 3, pp. 363–433, Academic Press, London, (1970).
Miller, Expts. in Mol. Genetics, pp. 235–245, Cold Spring Harbor Laboratory, Cold Spring Harbor, N.Y. (1972).

*Primary Examiner*—Mindy B. Fleisher
*Assistant Examiner*—Nancy T. Vogel
*Attorney, Agent, or Firm*—Oblon, Spivak, McClelland, Maier & Neustadt

[57] ABSTRACT

*E. coli* bacterial strains encoding a restriction gene that degrades methylated DNA, and prevents cloning of genes expressing the methyltransferase responsible for methylation, are mutated by a chemical or physical mutagen, so as to make the restriction enzyme temperature sensitive. Mutant cells are rendered competent, and plasmids expected or known to contain genes encoding methyltransferase enzymes are introduced. The transformants grow at the permissive temperature, where the restriction enzyme system is inactivated due to the mutated gene. Successful clones, expressing a methyltransferase, can be quickly identified by those which grow at the permissive temperature, but not at the non-permissive temperature. The valuable methyltransferases, as well as restriction enzymes associated therewith, can accordingly be recovered in large quantity.

15 Claims, No Drawings

MUTANT STRAIN OF *E. COLI* FOR DETECTION OF METHYLTRANSFERASE CLONES

This application is a Continuation of application Ser. No. 07/345,292, filed on May 1, 1989, now abandoned.

BACKGROUND OF THE INVENTION

1. Field of the Invention

This invention pertains to the production and recovery of methyltransferase enzymes from bacteria containing cloned genes expressing the same. More specifically, a method is provided for producing and detecting bacterial having cloned genes coding for and expressing methylase (methyltransferase) enzymes, cultivating those bacteria, and recovering the expressed product, without prior knowledge of the nature of the gene sequence encoding said methylase enzyme.

2. Background of the Prior Art

The increasing importance of DNA sequencing, particularly, large fragment production for the construction of artificial genes and the like, has increased the importance of methylase or methyltransferase enzymes. DNA methylation is a basic post-replication event that protects DNA (particularly endogenous DNA) from restriction enzymes. Additionally, genes encoding methylase enzymes are frequently associated with restriction enzymes, which recognize the same sequence that the methyltransferase recognizes. Both restriction enzymes and the enzymes responsible for methylation are critical tools of recombinant DNA technology.

However, commercial use of the methyltransferase enzymes, particularly known DNA sequence specific methyltransferases has been limited by the low levels associated with the expression of the enzymes, in the natural expression vehicles, which include a wide variety of bacteria. Desirably, the commercial availability and utility of these enzymes can be increased by cloning of the gene sequence encoding for DNA specific methyltransferases in expression vehicles, together with an appropriate promoter sequence, if necessary, and over expressing them in bacteria such as *E. coli*.

However, hybrid plasmids encoding methyltransferases are restricted by the presence of one of a triplet of restriction enzymes common to *E. coli* strains, encoded by the genes mcrA, mcrB, or mrr (Raleigh et al), *Proceedings of the National Academy of Science, U.S.A.*, 83 (1986). Specifically, it is believed that the presence of the restriction enzymes encoded by these genes are responsible for the degradation of the non-endogenous, "incoming" methylated plasmid DNA. Heitman et al, *Journal of Bacteriology*, 103 (1987).

Moreover, conventional gene cloning of DNA methylases depends on prior knowledge of the existence of the enzyme itself, and some information regarding the enzyme, or the gene responsible. Thus, in general, the cloning process begins with an identification of the DNA fragments encoding the enzyme or other protein in question. A DNA library is generated by use of restriction enzymes, dividing the original genome of the natural expression vehicle for the desired product at low levels into a plurality of gene fragments of different sizes.

These gene fragments are ligated into a cloning vector, and then taken up, by competent cells prepared according to conventional technology. The transformed cells are grown and tested for the presence of the desired activity.

As noted, a specific drawback of this process is that only predicted proteins, such as enzymes as to which there is considerable knowledge, can be obtained in this fashion. It is impossible, according to prior art processes, to rapidly identify unknown expressed DNA methylases in cloned hybrids, without exhaustive testing.

Accordingly, it remains an object of the art to provide a method whereby methyltransferases, both known and unstudied, can be successfully cloned into expression vehicles such as *E. coli*, and the methyltransferase expressed thereby recovered.

SUMMARY OF THE INVENTION

Successful introduction of plasmids encoding methyltransferase in *E. coli* of DNA plasmids encoding methyltransferase enzymes is achieved by using a temperature-sensitive mutated strain of *E. coli* capable of growing at the elevated temperature of about 42° C. but incapable of growth at a non-permissive temperature of about 30° C. The mutated *E. coli* can be obtained through any of a variety of mutation processes, including the introduction of chemical mutagens, direct or indirect irradiation of the *E. coli* parents with a radiative source, such UV radiation, cobalt 60 radiation, etc. Additional, chemical-type mutagens, such as intercolating agents, can also be used. In general, a wide variety of mutagens, such as those discussed by Friefelder, *Molecular Biology*, Chapter 11 (1987)can be used.

The cells surviving the mutagen exposure are grown overnight, at the permissive temperature, and prepared for uptake of a methyltransferase encoding plasmid. This plasmid is prepared to include a known gene, encoding a methyltransferase.

After overnight incubation at the permissive temperature, the resulting colonies are replica-plated, and incubated again, this time at both the permissive and non-permissive temperatures. Those colonies unable to grow at the non-permissive temperature but growing well at the permissive temperature have been transformed by plasmids carrying DNA encoding methyltransferases that methylate DNA recognized by the specific temperature sensitive restriction enzyme or enzymes present in the mutated strain. The mutant, transformed strain can be cultivated in order to recover the methyltransferase.

DETAILED DESCRIPTION OF THE INVENTION

The results obtained by the inventors herein strongly suggest that the mutation induced progeny exhibit a gene encoding a temperature-sensitive restriction enzyme system, be it an mcrB, mcrA or mrr restriction enzyme. The activity of this enzyme is expressed at the non-permissive temperature, e.g., about 30° C., but not at the permissive temperature, e.g., about 42° C. Thus, at the higher temperature, the cell can accept a plasmid comprising a gene encoding DNA methyltransferase, which methylates DNA recognized by the restriction nuclease present (e.g., mcrB nuclease). At 30° C., however, the restriction system is present and active and accordingly, inhibits growth of the cells, as discussed in detail above.

Thus, the system disclosed and claimed herein provides a quick and easy method for determining the presence in *E. coli* of plasmids expressing methyltransferases which methylate DNA such that the methylated material is sensitive to the restriction system active in the bacterial strain selected. Since each of the methylase-dependent restriction systems of *E. coli* recognizes a broad spectrum of methylated nucleotide sequences, they can be used to select a great number of DNA methyltransferase clones, each of which will recognize a different sequence. By replica plating the transformants, grown at 42° C. and 30° C., those unable to grow at 30° C. should possess the desired gene. Further, identification of a methyltransferase gene implies the identification of a gene for a restriction enzyme, as the two genes are generally paired. These genes can be reintroduced to a production strain, to recover the expressed product.

Of particular importance is the observation that this system does not require prior knowledge of the methyltransferase itself, or the gene sequence. Simple generation of a random DNA library, coupled with uptake by competent, mutated cells at the permissive temperature, followed by replica plating and attempted growth at the permissive and non-permissive temperature, should be sufficient to indicate whether or not the surviving transformant colonies encode a methyltransferase.

Once identified, the bacteria containing the clones may be cultivated at the identified temperature, and the desired expression product, the methyltransferase, recovered according to standard procedures (collection from the growth media, or directly from the organism). Additionally, the quick identification of plasmids encoding methyltransferases allows rapid and detailed study of the gene sequence itself, which may provide the opportunity to obtain non-natural sequences which are effective in producing more, highly active, transferase enzymes.

In order to demonstrate the utility of the invention, an *E. coli* strain with the mcrB restriction gene was selected and mutated, and competent cells transformed with a plasmid obtained from New England Biolabs containing a known, cloned gene for a methyltransferase, M.HaeIII. This same process can be duplicated, using alternative *E. coli* strains with the same or different restriction systems, and with plasmids known to contain a gene for a specific methyltransferase or genes of unknown characteristics. The example should therefore not be considered limiting in any way.

EXAMPLE

Isolation of an mcrB Temperature-Sensitive Mutant

To select for an mcrB temperature-sensitive mutant, *E. coli* MM294 strain (Raleigh and Wilson 1987) was mutagenized with NTG (200 µg/ml) essentially as described by Hubacek and Glover (1970). The surviving cells (approximately 0.1% survival) were grown overnight at 42° C., and 0.2 ml of this culture was used for preparation of the competent cells by the $CaCl_2$ procedure (Maniatis et al, *Molecular Cloning. A Laboratory Manual*, 1982), except that the cells were grown at 42° C. The competent cells were transformed with a pBR322 derivative containing a cloned gene for M.Hae III, kindly supplied by New England Biolabs. After 1 hour of growth at 42° C., the transformed cells were plated on LB plates containing 30 µg Ap/ml (prewarmed at 42° C.) and incubated overnight at 42° C. for 18 hours. The resulting transformant colonies (approximately 70) were replica-plated on LB+Ap plates and incubated overnight at 42° C. and 30° C. From two transformants that did not grow at 30° C., one name Apla was cured of pBR322::Hae III plasmid by growth in the presence of novobiocin (360 KµM), and its plasmid-free derivative Apla-10 was used for further studies.

Properties of the *Escherichia coli* Apla-10 Strain

The results presented in Table I show that the *E. coli* Apla [pBr322::M.HaeIII] strain has a greatly reduced ability to form colonies at 30° C., while its plasmid-free derivative forms the same number of colonies at both temperatures. This would suggest that the isolated Apla-10 strain does indeed carry a temperature-sensitive mutation in the mcrB gene. To test this assumption further, competent cells of the Apla-10 strain, grown at 42° C. and 30° C., were transformed with plasmid pBR322 carrying different DNA methyltransferase genes. As can be seen from the results present in Table II, all plasmids carrying DNA methyltransferases that render methylated DNA sensitive to the mcrB nuclease can transform the Apla-10 strain at 42° C. but are unable to transform it at 30° C. Moreover, transformant colonies obtained at 42° C. were unable to grow at 30°. On the other hand, Plasmid pSK5 carrying M.Hha II gene, which renders methylated NDA sensitive to mrr but not to the mcrB nuclease (Heitman and Model, 1987), cannot transform this strain at either temperature.

TABLE I

The ability of Apla and Apla-10 strains to form colonies in the presence of inactive (at 42° C.) and active (at 30248C) and mcrB restrictions systems.

| | Number Of Colonies Formed At:** | |
|---|---|---|
| Strains | 42° C. | 30° C. (As Compared With Those Formed At 42° C.) |
| MM294* | 1 | 1 |
| Apla[pBR322::M.HaeIII] | 1 | $10^{-5}$ |
| Apla-10 | 1 | 0.8 |

*for a description of strain properties see Raleigh and Wilson 1986.
**The bacterial cells were grown in LB medium to a density of $1 \times 10^8$ cells/ml at 42° C., diluted, plated on prewarmed LB agar plates, and incubated at the appropriate temperatures

TABLE II

Frequency of transformation of Apla-10 strain in the absence (42° C.) and Presence (30° C.) of the mcrB system

| | | Relative Frequency of Transformation * | |
|---|---|---|---|
| Plasmid | Sequence Recognized By the Methyltransferase | 42° C. | 30° C. As Compared with Those Formed at 42° C. |
| pBR322::M.HaeIII ** | GGCC | 0.85 | $<10^{-4}$ |
| pBR322::M.HaeII ** | PUGCGCPY | 0.70 | $<10^{-4}$ |

TABLE II-continued

Frequency of transformation of Apla-10 strain in the absence (42° C.) and Presence (30° C.) of the mcrB system

| Plasmid | Sequence Recognized By the Methyltransferase | Relative Frequency of Transformation * | |
|---|---|---|---|
| | | 42° C. | 30° C. As Compared with Those Formed at 42° C. |
| pH56::M.NgoIV **** | GCCGGC | 0.5 | $<10^{-4}$ |
| pBR322::M.NlaIV ** | GGNNCC | 0.85 | $<10^{-4}$ |
| pSK5(M.HhaII) *** | GANTC | $<10^{-4}$ | $<10^{-4}$ |
| pBR322 | — | 1 | 1 |
| pACYC184 | — | 1 | 1 |

* Transformations were performed by adding 0.1 g to 0.1 ml of competent cells ($5 \times 10^7$ cells). Transformation frequency of 1 corresponds to approximately $4 \times 10^5$ transformant/μg of DNA.
** Plasmids carrying M.HaeII, M.HaeIII and M.NlaIV genes were kindly supplied by New England Biolabs
*** Plasmid pSK5 was kindly supplied by Dr. H. Smith
**** Plasmid pH56::M.NgoIV was kindly supplied by Dr. H. Siefert The invention described above has been disclosed with reference to general description and specific example. Obviously alterations from the specific examples set forth, and the exemplary description, can be introduced, without departing from the invention disclosed herein as claimed below. In particular, mutagens, temperatures, growth media and the like, other than those set forth above, can be employed without the exercise of inventive facility. Additionally, specific and selective combinations of particular bacterial strains, gene sequences and the like, are embraced by the invention save for the limits placed on the invention by the claims appended hereto. Nothing in the specification is intended as limiting, unless specifically so indicated.

What is claimed is:

1. A method for detecting *E. coli* bacterial cells containing a cloned methyltransferase gene, said cells expressing a methyltransferase enzyme, comprising:

transforming an *E. coli* bacterial cell having a gene encoding the production of a temperature sensitive DNA restriction enzyme reactive with DNA methylated by said methyltransferase, by combining said cell with a plasmid encoding said methyltransferase, said enzymae being active at a first temperature range termed the non-permissive temperature and inactive at a second temperature range termed the permissive temperature, cultivating said cell at both said permissive and non-permissive temperature ranges, wherein cells which grow at said permissive temperature range and do not grow at said non-permissive temperature range are expressing said methyltransferase.

2. The method of claim 1, wherein the gene sequence for said methyltransferase is known.

3. The method of claim 1, wherein the gene sequence for said methyltransferase is unknown.

4. A method for producing methyltransferase, comprising:

transforming *E. coli* bacterial cells having a gene encoding the production of a temperature-sensitive DNA restriction enzyme reactive with DNA methylated by said methyltransferase, by combining said bacterial cells with a plasmid encoding said methyltransferase, said temperature sensitive restriction enzyme being inactive at a temperature range at which the cells can grow and multiply, and, cultivating said cells at said temperature range, and recovering the methyltransferase expressed by said cells.

5. The method of claim 4, wherein said bacterial cells and cultivated at about 42° C.

6. The method of claim 4, wherein said bacterial cells are grown on a nutrient medium, and said methyltransferase is recovered from said medium.

7. The method of claim 4, wherein said bacterial cells are harvested, and said methyltransferase is obtained directly from said cells.

8. A method of producing mutant, temperature sensitive *E. coli* bacteria capable of expressing a methyltransferase enzyme, comprising:

exposing *E. coli* bacteria having a restriction enzyme gene, selected from the group consisting of mcrA, mcrB and mrr, to a mutagen, cultivating the bacteria surviving exposure to said mutagen at a first temperature range, termed the permissive temperature range, at which the gene corresponding to said restriction enzyme gene is inactive, but the bacteria continue to grow, and transforming said cultivated bacteria with a plasmid encoding a methyltransferase capable of methylating DNA to which said restriction enzyme is reactive, incubating said transformed, mutant bacteria, and attempting to grow the resulting cells at said permissive temperature range, and a second temperature range, at which said restriction enzyme gene is active, termed the non-permissive temperature range, wherein said cells which grow at said permissive temperature range, but not at said non-permissive temperature range express said methyltransferase.

9. The method of claim 8, wherein said mutagen is a chemical mutagen.

10. The method of claim 9, wherein said chemical mutagen comprises N-methyl-N-nitro-N-nitrosoguanidine.

11. The method of claim 8, wherein said mutagen comprises a non-chemical mutagen.

12. The method of claim 8, wherein said restriction enzyme is inactive at about 42° C., and said restriction enzyme is active at about 30° C.

13. An *E. coli* novel bacterial cell, having a genome comprising a plasmid which encodes a methyltransferase, said genome further comprising a gene encoding a temperature sensitive restriction enzyme reactive with methylated DNA produced by said methyltransferase, the restriction enzyme being active at a first, non-permissive temperature range, and inactive at a second, permissive temperature range, wherein said bacterial cell can grow at said permissive temperature range, but not at said non-permissive temperature range.

14. The bacterial cell of claim 13, wherein said bacterial cell is an *E. coli* bacterial cell mutated by exposure to a mutagen.

15. The method of claim 1, wherein identification of a methyltransferase encoding transformant indicates the transformant also contains a gene encoding a restriction enzyme associated with said gene encoding said methyltransferase.

* * * * *